(12) United States Patent
Fulkerson et al.

(10) Patent No.: US 9,759,710 B2
(45) Date of Patent: *Sep. 12, 2017

(54) MODULAR RESERVOIR ASSEMBLY FOR A HEMODIALYSIS AND HEMOFILTRATION SYSTEM

(71) Applicant: Fresenius Medical Care Holdings, Inc., Waltham, MA (US)

(72) Inventors: Barry Neil Fulkerson, Longmont, CO (US); Mark Smith, Longmont, CO (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/923,904

(22) Filed: Oct. 27, 2015

(65) Prior Publication Data

US 2016/0109429 A1    Apr. 21, 2016

Related U.S. Application Data

(63) Continuation of application No. 12/751,930, filed on Mar. 31, 2010, now Pat. No. 9,199,022, and a
(Continued)

(51) Int. Cl.
*A61M 1/16* (2006.01)
*G01N 33/487* (2006.01)
(Continued)

(52) U.S. Cl.
CPC ....... *G01N 33/48707* (2013.01); *A61M 1/166* (2014.02); *A61M 1/1621* (2014.02);
(Continued)

(58) Field of Classification Search
CPC .................................................. A61M 1/1656
See application file for complete search history.

(56) References Cited

U.S. PATENT DOCUMENTS 2,276,843 A    3/1942 Hathaway
2,328,381 A    8/1943 Jaffe
(Continued)

FOREIGN PATENT DOCUMENTS

CN    1235849 A    11/1999
CN    1471617 A    1/2004
(Continued)

OTHER PUBLICATIONS

First Office Action for Canadian Patent Application No. CA2749171, dated Jan. 8, 2016.
(Continued)

*Primary Examiner* — Peter Keyworth
(74) *Attorney, Agent, or Firm* — Novel IP

(57) ABSTRACT

The present specification discloses a dialysis system having a reservoir module with a reservoir housing defining an internal space, a surface located within the internal space for supporting a container that contains dialysate, and a conductivity sensor located within the internal space, where the conductivity sensor has a coil, a capacitor in electrical communication with the coil, and an energy source in electrical communication with the circuit.

18 Claims, 8 Drawing Sheets

Related U.S. Application Data continuation-in-part of application No. 12/610,032, filed on Oct. 30, 2009, now abandoned.

(60) Provisional application No. 61/165,389, filed on Mar. 31, 2009, provisional application No. 61/109,834, filed on Oct. 30, 2008.

(51) Int. Cl.
*A61M 1/34* (2006.01)
*G01N 27/22* (2006.01)

(52) U.S. Cl.
CPC ........ *A61M 1/1656* (2013.01); *A61M 1/1664* (2014.02); *A61M 1/34* (2013.01); *G01N 27/221* (2013.01); *G01N 27/228* (2013.01); *A61M 2205/15* (2013.01); *A61M 2205/3317* (2013.01); *A61M 2205/3393* (2013.01); *A61M 2205/36* (2013.01); *A61M 2209/084* (2013.01)

(56) References Cited

U.S. PATENT DOCUMENTS

| | | | |
|---|---|---|---|
| 2,569,105 A | 9/1951 | James | |
| 2,977,791 A | 4/1961 | Dubsky | |
| 3,200,591 A | 8/1965 | Ray | |
| 3,216,281 A | 11/1965 | Teichert | |
| 3,242,456 A | 3/1966 | Duncan | |
| 3,308,798 A | 3/1967 | Snider | |
| 3,388,803 A | 6/1968 | Scott | |
| 3,420,492 A | 1/1969 | Ray | |
| 3,464,448 A | 9/1969 | Schmitz | |
| 3,511,469 A | 5/1970 | Bell | |
| 3,514,674 A | 5/1970 | Ito | |
| 3,669,878 A | 6/1972 | Marantz | |
| 3,669,880 A | 6/1972 | Marantz | |
| 3,709,222 A | 1/1973 | De Vries | |
| 3,728,654 A | 4/1973 | Tada | |
| 3,746,175 A | 7/1973 | Markley | |
| 3,752,189 A | 8/1973 | Marr | |
| 3,803,913 A | 4/1974 | Tracer | |
| 3,814,376 A | 6/1974 | Reinicke | |
| 3,850,835 A | 11/1974 | Marantz | |
| 3,884,808 A | 5/1975 | Scott | |
| 3,894,431 A | 7/1975 | Muston | |
| 3,902,490 A | 9/1975 | Jacobsen | |
| 3,946,731 A | 3/1976 | Lichtenstein | |
| 3,961,918 A | 6/1976 | Johnson | |
| 3,983,361 A | 9/1976 | Wild | |
| 3,989,622 A | 11/1976 | Marantz | |
| 3,989,625 A | 11/1976 | Mason | |
| 3,994,799 A | 11/1976 | Yao | |
| 4,000,072 A | 12/1976 | Sato | |
| 4,047,099 A * | 9/1977 | Berger | G01N 27/06 324/118 |
| 4,071,444 A | 1/1978 | Ash | |
| 4,083,777 A | 4/1978 | Hutchisson | |
| 4,094,775 A | 6/1978 | Mueller | |
| 4,113,614 A | 9/1978 | Rollo | |
| 4,118,314 A | 10/1978 | Yoshida | |
| 4,155,852 A | 5/1979 | Fischel | |
| 4,209,392 A | 6/1980 | Wallace | |
| 4,212,738 A | 7/1980 | Henne | |
| 4,247,393 A | 1/1981 | Wallace | |
| 4,253,493 A | 3/1981 | English | |
| 4,259,985 A | 4/1981 | Bergmann | |
| 4,267,040 A | 5/1981 | Schael | |
| 4,269,708 A | 5/1981 | Bonomini | |
| 4,326,955 A | 4/1982 | Babb | |
| 4,348,283 A | 9/1982 | Ash | |
| 4,354,562 A | 10/1982 | Newman | |
| 4,368,737 A | 1/1983 | Ash | |
| 4,371,385 A | 2/1983 | Johnson | |
| 4,381,999 A | 5/1983 | Boucher | |
| 4,387,777 A | 6/1983 | Ash | |
| 4,397,189 A | 8/1983 | Johnson | |
| 4,397,519 A | 8/1983 | Cooney | |
| 4,402,694 A | 9/1983 | Ash | |
| 4,403,765 A | 9/1983 | Fisher | |
| 4,403,984 A | 9/1983 | Ash | |
| 4,413,988 A | 11/1983 | Handt | |
| 4,430,098 A | 2/1984 | Bowman | |
| 4,443,333 A | 4/1984 | Mahurkar | |
| 4,460,555 A | 7/1984 | Thompson | |
| 4,464,172 A | 8/1984 | Lichtenstein | |
| 4,466,804 A | 8/1984 | Hino | |
| 4,469,593 A | 9/1984 | Ishihara | |
| 4,477,342 A | 10/1984 | Allan | |
| 4,480,483 A | 11/1984 | McShane | |
| 4,498,902 A | 2/1985 | Ash | |
| 4,531,799 A | 7/1985 | Gray | |
| 4,535,637 A | 8/1985 | Feller | |
| 4,559,039 A | 12/1985 | Ash | |
| 4,563,170 A | 1/1986 | Aigner | |
| 4,581,141 A | 4/1986 | Ash | |
| 4,586,576 A | 5/1986 | Inoue | |
| 4,596,550 A | 6/1986 | Troutner | |
| 4,599,055 A | 7/1986 | Dykstra | |
| 4,606,826 A | 8/1986 | Sano | |
| 4,630,799 A | 12/1986 | Nolan | |
| 4,650,587 A | 3/1987 | Polak | |
| 4,661,246 A | 4/1987 | Ash | |
| 4,666,598 A | 5/1987 | Heath | |
| 4,680,122 A | 7/1987 | Barone | |
| 4,683,053 A | 7/1987 | Polaschegg | |
| 4,710,164 A | 12/1987 | Levin | |
| 4,731,072 A | 3/1988 | Aid | |
| 4,740,755 A | 4/1988 | Ogawa | |
| 4,750,705 A | 6/1988 | Zippe | |
| 4,762,618 A | 8/1988 | Gummesson | |
| 4,765,421 A | 8/1988 | Newton | |
| 4,765,907 A | 8/1988 | Scott | |
| 4,777,953 A | 10/1988 | Ash | |
| 4,806,247 A | 2/1989 | Schoendorfer | |
| 4,808,089 A | 2/1989 | Buchholtz | |
| 4,826,663 A | 5/1989 | Alberti | |
| 4,828,543 A | 5/1989 | Weiss | |
| 4,828,693 A | 5/1989 | Lindsay | |
| 4,831,884 A | 5/1989 | Drenthen | |
| 4,854,322 A | 8/1989 | Ash | |
| 4,861,242 A | 8/1989 | Finsterwald | |
| 4,881,839 A | 11/1989 | Grimm | |
| 4,882,937 A | 11/1989 | Leon | |
| 4,885,942 A | 12/1989 | Magori | |
| 4,894,164 A | 1/1990 | Polaschegg | |
| 4,897,189 A | 1/1990 | Greenwood | |
| 4,909,713 A | 3/1990 | Finsterwald | |
| 4,914,819 A | 4/1990 | Ash | |
| 4,943,279 A | 7/1990 | Samiotes | |
| 4,950,244 A | 8/1990 | Fellingham | |
| 4,950,395 A | 8/1990 | Richalley | |
| 4,968,422 A | 11/1990 | Runge | |
| 4,985,015 A | 1/1991 | Obermann | |
| 4,990,258 A | 2/1991 | Bjare | |
| 4,995,268 A | 2/1991 | Ash | |
| 4,997,570 A | 3/1991 | Polaschegg | |
| 5,000,274 A | 3/1991 | Bullivant | |
| 5,002,054 A | 3/1991 | Ash | |
| 5,009,101 A | 4/1991 | Branam | |
| 5,011,607 A | 4/1991 | Shinzato | |
| 5,032,261 A | 7/1991 | Pyper | |
| 5,074,368 A | 12/1991 | Bullivant | |
| 5,100,554 A | 3/1992 | Polaschegg | |
| 5,114,580 A | 5/1992 | Ahmad | |
| 5,138,138 A | 8/1992 | Theilacker | |
| 5,147,613 A | 9/1992 | Heilmann | |
| 5,152,174 A | 10/1992 | LaBudde | |
| 5,157,332 A * | 10/1992 | Reese | G01R 27/22 324/204 |
| 5,161,779 A | 11/1992 | Graner | |
| 5,170,789 A | 12/1992 | Narayan | |
| 5,188,604 A | 2/1993 | Orth | |
| 5,198,335 A | 3/1993 | Sekikawa | |
| 5,211,643 A | 5/1993 | Reinhardt | |

(56) References Cited

U.S. PATENT DOCUMENTS

| | | | |
|---|---|---|---|
| 5,215,450 A | 6/1993 | Tamari | |
| 5,220,843 A | 6/1993 | Rak | |
| 5,228,308 A | 7/1993 | Day | |
| 5,230,341 A | 7/1993 | Polaschegg | |
| 5,230,614 A | 7/1993 | Zanger | |
| 5,258,127 A | 11/1993 | Gsell | |
| 5,259,961 A | 11/1993 | Eigendorf | |
| 5,277,820 A | 1/1994 | Ash | |
| 5,284,470 A | 2/1994 | Beltz | |
| 5,284,559 A | 2/1994 | Lim | |
| 5,295,505 A | 3/1994 | Polaschegg | |
| 5,304,349 A | 4/1994 | Polaschegg | |
| 5,308,315 A | 5/1994 | Khuri | |
| 5,322,258 A | 6/1994 | Bosch | |
| 5,322,519 A | 6/1994 | Ash | |
| 5,346,472 A | 9/1994 | Keshaviah | |
| 5,347,115 A | 9/1994 | Sherman | |
| 5,352,364 A | 10/1994 | Kruger | |
| 5,360,445 A | 11/1994 | Goldowsky | |
| 5,385,005 A | 1/1995 | Ash | |
| D355,816 S | 2/1995 | Ash | |
| 5,391,143 A | 2/1995 | Kensey | |
| 5,405,315 A | 4/1995 | Khuri | |
| 5,405,320 A | 4/1995 | Twardowski | |
| 5,408,576 A | 4/1995 | Bishop | |
| 5,415,532 A | 5/1995 | Loughnane | |
| 5,441,636 A | 8/1995 | Chevallet | |
| 5,445,630 A | 8/1995 | Richmond | |
| 5,460,493 A | 10/1995 | Deniega | |
| 5,468,388 A | 11/1995 | Goddard | |
| 5,469,737 A | 11/1995 | Smith | |
| 5,476,444 A | 12/1995 | Keeling | |
| 5,518,015 A | 5/1996 | Berget | |
| D370,531 S | 6/1996 | Ash | |
| 5,536,412 A | 7/1996 | Ash | |
| 5,540,265 A | 7/1996 | Polaschegg | |
| 5,545,131 A | 8/1996 | Davankov | |
| 5,577,891 A | 11/1996 | Loughnane | |
| 5,580,460 A | 12/1996 | Polaschegg | |
| 5,591,344 A | 1/1997 | Kenley | |
| 5,609,770 A | 3/1997 | Zimmerman | |
| 5,614,677 A | 3/1997 | Wamsiedler | |
| 5,616,305 A | 4/1997 | Mathieu | |
| 5,624,551 A | 4/1997 | Baumann | |
| 5,624,572 A | 4/1997 | Larson | |
| 5,629,871 A | 5/1997 | Love | |
| 5,632,897 A | 5/1997 | Mathieu | |
| 5,644,285 A | 7/1997 | Maurer | |
| 5,650,704 A | 7/1997 | Pratt | |
| 5,674,390 A | 10/1997 | Matthews | |
| 5,679,245 A | 10/1997 | Manica | |
| 5,690,821 A * | 11/1997 | Kenley | A61L 2/04 210/195.1 |
| 5,693,008 A | 12/1997 | Brugger | |
| 5,698,083 A | 12/1997 | Glass | |
| 5,711,883 A | 1/1998 | Folden | |
| 5,713,850 A | 2/1998 | Heilmann | |
| 5,725,773 A | 3/1998 | Polaschegg | |
| 5,725,776 A | 3/1998 | Kenley | |
| 5,744,027 A | 4/1998 | Connell | |
| 5,762,782 A | 6/1998 | Kenley | |
| 5,770,806 A | 6/1998 | Hiismaeki | |
| 5,782,796 A | 7/1998 | Din | |
| 5,794,669 A | 8/1998 | Polaschegg | |
| 5,840,068 A | 11/1998 | Cartledge | |
| 5,858,186 A | 1/1999 | Glass | |
| 5,876,419 A | 3/1999 | Carpenter | |
| 5,902,336 A | 5/1999 | Mishkin | |
| 5,906,978 A | 5/1999 | Ash | |
| 5,919,369 A | 7/1999 | Ash | |
| 5,928,177 A | 7/1999 | Brugger | |
| 5,938,938 A | 8/1999 | Bosetto | |
| 5,944,684 A | 8/1999 | Roberts | |
| 5,945,343 A | 8/1999 | Munkholm | |
| 5,947,953 A | 9/1999 | Ash | |
| 5,951,870 A | 9/1999 | Utterberg | |
| 5,980,481 A | 11/1999 | Gorsuch | |
| 5,984,891 A | 11/1999 | Keilman | |
| 5,989,423 A | 11/1999 | Kamen | |
| 5,989,438 A | 11/1999 | Fumiyama | |
| 6,012,342 A | 1/2000 | Blight | |
| 6,042,561 A | 3/2000 | Ash | |
| 6,044,691 A | 4/2000 | Kenley | |
| 6,047,108 A | 4/2000 | Sword | |
| 6,062,256 A | 5/2000 | Miller | |
| 6,069,343 A | 5/2000 | Kolowich | |
| 6,086,753 A | 7/2000 | Ericson | |
| 6,116,269 A | 9/2000 | Maxson | |
| 6,117,100 A | 9/2000 | Powers | |
| 6,117,122 A | 9/2000 | Din | |
| 6,156,007 A | 12/2000 | Ash | |
| 6,168,578 B1 | 1/2001 | Diamond | |
| 6,190,349 B1 | 2/2001 | Ash | |
| 6,196,922 B1 | 3/2001 | Hantschk | |
| 6,196,992 B1 | 3/2001 | Keilman | |
| 6,200,485 B1 | 3/2001 | Kitaevich | |
| 6,217,540 B1 | 4/2001 | Yazawa | |
| 6,228,047 B1 | 5/2001 | Dadson | |
| 6,234,989 B1 | 5/2001 | Brierton | |
| 6,240,789 B1 | 6/2001 | Morlan | |
| 6,254,567 B1 | 7/2001 | Treu | |
| 6,264,611 B1 | 7/2001 | Ishikawa | |
| 6,264,680 B1 | 7/2001 | Ash | |
| 6,280,406 B1 | 8/2001 | Dolcek | |
| 6,284,131 B1 | 9/2001 | Hogard | |
| 6,287,516 B1 | 9/2001 | Matson | |
| 6,289,749 B1 | 9/2001 | Sanders | |
| 6,303,036 B1 | 10/2001 | Collins | |
| 6,325,774 B1 | 12/2001 | Bene | |
| 6,332,985 B1 | 12/2001 | Sherman | |
| 6,341,758 B1 | 1/2002 | Shih | |
| 6,348,162 B1 | 2/2002 | Ash | |
| 6,354,565 B1 | 3/2002 | Doust | |
| 6,406,631 B1 | 6/2002 | Collins | |
| 6,409,699 B1 | 6/2002 | Ash | |
| 6,416,293 B1 | 7/2002 | Bouchard | |
| 6,468,427 B1 | 10/2002 | Frey | |
| 6,471,872 B2 | 10/2002 | Kitaevich | |
| 6,487,904 B1 | 12/2002 | Myhre | |
| 6,491,656 B1 | 12/2002 | Morris | |
| 6,491,673 B1 | 12/2002 | Palumbo | |
| 6,497,675 B1 | 12/2002 | Davankov | |
| 6,517,044 B1 | 2/2003 | Lin | |
| 6,517,045 B1 | 2/2003 | Northedge | |
| 6,551,513 B2 | 4/2003 | Nikaido | |
| 6,554,789 B1 | 4/2003 | Brugger | |
| 6,561,997 B1 | 5/2003 | Weitel | |
| 6,565,395 B1 | 5/2003 | Schwarz | |
| 6,572,576 B2 | 6/2003 | Brugger | |
| 6,572,641 B2 | 6/2003 | Brugger | |
| 6,579,253 B1 | 6/2003 | Burbank | |
| 6,579,460 B1 | 6/2003 | Willis | |
| 6,582,385 B2 | 6/2003 | Burbank | |
| 6,589,482 B1 | 7/2003 | Burbank | |
| 6,595,943 B1 | 7/2003 | Burbank | |
| 6,607,495 B1 | 8/2003 | Skalak | |
| 6,610,036 B2 | 8/2003 | Branch | |
| 6,623,470 B2 | 9/2003 | Munis | |
| 6,627,164 B1 | 9/2003 | Wong | |
| 6,632,192 B2 | 10/2003 | Gorsuch | |
| 6,638,477 B1 | 10/2003 | Treu | |
| 6,638,478 B1 | 10/2003 | Treu | |
| 6,649,063 B2 | 11/2003 | Brugger | |
| 6,653,841 B1 | 11/2003 | Koerdt | |
| 6,673,314 B1 | 1/2004 | Burbank | |
| 6,681,624 B2 | 1/2004 | Furuki | |
| 6,685,664 B2 | 2/2004 | Levin | |
| 6,690,280 B2 | 2/2004 | Citrenbaum | |
| 6,695,803 B1 | 2/2004 | Robinson | |
| 6,702,561 B2 | 3/2004 | Stillig | |
| 6,706,007 B2 | 3/2004 | Gelfand | |
| 6,730,266 B2 | 5/2004 | Matson | |
| 6,743,193 B2 | 6/2004 | Brugger | |
| 6,752,172 B2 | 6/2004 | Lauer | |

(56) References Cited

U.S. PATENT DOCUMENTS

| | | |
|---|---|---|
| 6,758,975 B2 | 7/2004 | Peabody |
| 6,764,460 B2 | 7/2004 | Dolecek |
| 6,773,412 B2 | 8/2004 | OMahony |
| 6,776,912 B2 | 8/2004 | Baurmeister |
| 6,796,955 B2 | 9/2004 | OMahony |
| 6,818,196 B2 | 11/2004 | Wong |
| 6,830,553 B1 | 12/2004 | Burbank |
| 6,836,201 B1 | 12/2004 | Devenyi |
| 6,841,172 B1 | 1/2005 | Ash |
| 6,843,779 B1 | 1/2005 | Andrysiak |
| 6,852,090 B2 | 2/2005 | Burbank |
| 6,872,346 B2 | 3/2005 | Stillig |
| 6,878,283 B2 | 4/2005 | Thompson |
| 6,890,315 B1 | 5/2005 | Levin |
| 6,899,691 B2 | 5/2005 | Bainbridge |
| 6,923,782 B2 | 8/2005 | OMahony |
| 6,948,697 B2 | 9/2005 | Herbert |
| 6,955,655 B2 | 10/2005 | Burbank |
| 6,958,049 B1 | 10/2005 | Ash |
| 6,960,179 B2 | 11/2005 | Gura |
| 6,960,328 B2 | 11/2005 | Bortun |
| 6,979,309 B2 | 12/2005 | Burbank |
| 7,004,924 B1 | 2/2006 | Brugger |
| 7,007,549 B2 | 3/2006 | Kwon |
| 7,033,498 B2 | 4/2006 | Wong |
| 7,037,428 B1 | 5/2006 | Robinson |
| 7,040,142 B2 | 5/2006 | Burbank |
| 7,059,195 B1 | 6/2006 | Liu |
| 7,087,026 B2 | 8/2006 | Callister |
| 7,087,033 B2 | 8/2006 | Brugger |
| 7,097,148 B2 | 8/2006 | DeWall |
| 7,101,519 B2 | 9/2006 | Wong |
| 7,112,273 B2 | 9/2006 | Weigel |
| 7,115,095 B2 | 10/2006 | Egler |
| 7,135,156 B2 | 11/2006 | Hai |
| 7,144,386 B2 | 12/2006 | Korkor |
| 7,146,861 B1 | 12/2006 | Cook |
| 7,147,613 B2 | 12/2006 | Burbank |
| 7,169,303 B2 | 1/2007 | Sullivan |
| 7,175,809 B2 | 2/2007 | Gelfand |
| 7,214,312 B2 | 5/2007 | Brugger |
| 7,226,538 B2 | 6/2007 | Brugger |
| 7,241,272 B2 | 7/2007 | Karoor |
| 7,252,767 B2 | 8/2007 | Bortun |
| 7,267,658 B2 | 9/2007 | Treu |
| 7,270,015 B1 | 9/2007 | Feller |
| 7,273,465 B2 | 9/2007 | Ash |
| 7,276,042 B2 | 10/2007 | Polaschegg |
| 7,300,413 B2 | 11/2007 | Burbank |
| 7,309,323 B2 | 12/2007 | Gura |
| 7,314,208 B1 | 1/2008 | Rightley |
| 7,317,967 B2 | 1/2008 | DiGianfilippo |
| 7,332,096 B2 | 2/2008 | Blickhan |
| 7,337,674 B2 | 3/2008 | Burbank |
| 7,338,460 B2 | 3/2008 | Burbank |
| 7,347,849 B2 | 3/2008 | Brugger |
| 7,351,218 B2 | 4/2008 | Bene |
| 7,387,022 B1 | 6/2008 | Korniyenko |
| 7,494,590 B2 | 2/2009 | Felding |
| 7,531,098 B2 | 5/2009 | Robinson |
| 7,566,432 B2 | 7/2009 | Wong |
| 7,597,677 B2 | 10/2009 | Gura |
| 7,605,710 B2 | 10/2009 | Crnkovich |
| 7,618,531 B2 | 11/2009 | Sugioka |
| 7,628,378 B2 | 12/2009 | Adams |
| 7,645,253 B2 | 1/2010 | Gura |
| 7,648,476 B2 | 1/2010 | Bock |
| 7,696,762 B2 | 4/2010 | Quackenbush |
| 7,713,226 B2 | 5/2010 | Ash |
| 7,736,507 B2 | 6/2010 | Wong |
| 7,755,488 B2 | 7/2010 | Dvorsky |
| 7,766,873 B2 | 8/2010 | Moberg |
| 7,776,210 B2 | 8/2010 | Rosenbaum |
| 7,780,619 B2 | 8/2010 | Brugger |
| 7,794,141 B2 | 9/2010 | Perry |
| 7,873,489 B2 | 1/2011 | Dolgos |
| 7,874,999 B2 | 1/2011 | Busby |
| 7,886,611 B2 | 2/2011 | OMahony |
| 7,896,829 B2 | 3/2011 | Gura |
| 7,901,376 B2 | 3/2011 | Steck |
| 7,922,898 B2 | 4/2011 | Jonsson |
| 7,922,899 B2 | 4/2011 | Vasta |
| 7,935,074 B2 | 5/2011 | Plahey |
| 7,959,129 B2 | 6/2011 | Matsumoto |
| 7,981,082 B2 | 7/2011 | Wang |
| 7,981,280 B2 | 7/2011 | Carr |
| 7,995,816 B2 | 8/2011 | Roger |
| 7,998,101 B2 | 8/2011 | Ash |
| 8,021,319 B2 | 9/2011 | Delnevo |
| 8,029,454 B2 | 10/2011 | Kelly |
| 8,034,161 B2 | 10/2011 | Gura |
| 8,034,235 B2 | 10/2011 | Rohde |
| 8,062,513 B2 | 11/2011 | Yu |
| 8,066,658 B2 | 11/2011 | Karoor |
| 8,070,707 B2 | 12/2011 | Gelfand |
| 8,075,509 B2 | 12/2011 | Molducci |
| 8,078,333 B2 | 12/2011 | Kienman |
| 8,083,677 B2 | 12/2011 | Rohde |
| 8,105,260 B2 | 1/2012 | Tonelli |
| 8,105,487 B2 | 1/2012 | Fulkerson |
| 8,114,288 B2 | 2/2012 | Robinson |
| 8,118,276 B2 | 2/2012 | Sanders |
| 8,142,383 B2 | 3/2012 | Dannenmaier |
| 8,152,751 B2 | 4/2012 | Roger |
| 8,187,184 B2 | 5/2012 | Muller |
| 8,197,431 B2 | 6/2012 | Bennison |
| 8,221,320 B2 | 7/2012 | Bouton |
| 8,240,636 B2 | 8/2012 | Smith |
| 8,273,049 B2 * | 9/2012 | Demers |
| 8,323,492 B2 | 12/2012 | Childers |
| 8,342,478 B1 | 1/2013 | Cordray |
| 8,376,978 B2 | 2/2013 | Roger |
| 8,449,487 B2 | 5/2013 | Hovland |
| 8,491,184 B2 | 7/2013 | Kamen |
| 8,696,626 B2 | 4/2014 | Kirsch |
| 2002/0068364 A1 | 6/2002 | Arai |
| 2002/0085951 A1 | 7/2002 | Gelfand |
| 2002/0112609 A1 | 8/2002 | Wong |
| 2002/0113016 A1 | 8/2002 | Takai |
| 2002/0147423 A1 | 10/2002 | Burbank |
| 2002/0158019 A1 | 10/2002 | Collins |
| 2002/0187069 A1 | 12/2002 | Levin |
| 2002/0193679 A1 | 12/2002 | Malave |
| 2003/0012905 A1 | 1/2003 | Zumbrum |
| 2003/0048185 A1 | 3/2003 | Citrenbaum |
| 2003/0056585 A1 | 3/2003 | Furuki |
| 2003/0113931 A1 | 6/2003 | Pan |
| 2003/0113932 A1 | 6/2003 | Sternberg |
| 2003/0128125 A1 | 7/2003 | Burbank |
| 2003/0216677 A1 | 11/2003 | Pan |
| 2003/0220598 A1 | 11/2003 | Busby |
| 2003/0220606 A1 | 11/2003 | Busby |
| 2003/0236482 A1 | 12/2003 | Gorsuch |
| 2004/0019312 A1 | 1/2004 | Childers |
| 2004/0021108 A1 | 2/2004 | Hallback |
| 2004/0031756 A1 | 2/2004 | Suzuki |
| 2004/0167465 A1 | 8/2004 | Mihai |
| 2005/0070837 A1 | 3/2005 | Ferrarini |
| 2005/0086008 A1 | 4/2005 | DiGianfilippo |
| 2005/0101901 A1 | 5/2005 | Gura |
| 2005/0131332 A1* | 6/2005 | Kelly ................ A61M 1/1696 604/4.01 |
| 2005/0133439 A1 | 6/2005 | Blickhan |
| 2005/0150309 A1 | 7/2005 | Beard |
| 2005/0209547 A1 | 9/2005 | Burbank |
| 2005/0230292 A1 | 10/2005 | Beden |
| 2005/0240233 A1 | 10/2005 | Lippert |
| 2006/0064053 A1 | 3/2006 | Bollish |
| 2006/0117859 A1 | 6/2006 | Liu |
| 2006/0122552 A1 | 6/2006 | OMahony |
| 2006/0195064 A1 | 8/2006 | Plahey |
| 2006/0226057 A1 | 10/2006 | Robinson |
| 2006/0241543 A1 | 10/2006 | Gura |
| 2006/0289342 A1 | 12/2006 | Sugioka |

(56) References Cited

U.S. PATENT DOCUMENTS

| | | |
|---|---|---|
| 2007/0060786 A1 | 3/2007 | Gura |
| 2007/0112297 A1 | 5/2007 | Plahey |
| 2007/0158249 A1 | 7/2007 | Ash |
| 2007/0158268 A1 | 7/2007 | DeComo |
| 2007/0161113 A1 | 7/2007 | Ash |
| 2007/0179425 A1 | 8/2007 | Gura |
| 2007/0213654 A1 | 9/2007 | Lundtveit |
| 2007/0276328 A1* | 11/2007 | Childers ............ A61M 1/28 604/131 |
| 2008/0006570 A1 | 1/2008 | Gura |
| 2008/0021366 A1 | 1/2008 | Gura |
| 2008/0041136 A1 | 2/2008 | Kopelman |
| 2008/0041792 A1 | 2/2008 | Crnkovich |
| 2008/0051689 A1 | 2/2008 | Gura |
| 2008/0058696 A1 | 3/2008 | Gura |
| 2008/0065006 A1 | 3/2008 | Roger |
| 2008/0077068 A1 | 3/2008 | Orr |
| 2008/0149563 A1 | 6/2008 | Ash |
| 2008/0195021 A1 | 8/2008 | Roger |
| 2008/0195060 A1 | 8/2008 | Roger |
| 2008/0208103 A1 | 8/2008 | Demers |
| 2008/0217245 A1 | 9/2008 | Rambod |
| 2008/0230450 A1* | 9/2008 | Burbank ............ A61M 1/1656 210/92 |
| 2008/0258735 A1 | 10/2008 | Quackenbush |
| 2008/0264498 A1 | 10/2008 | Thompson |
| 2008/0290974 A1 | 11/2008 | Adams |
| 2009/0004053 A1 | 1/2009 | Kenley |
| 2009/0008306 A1 | 1/2009 | Cicchello |
| 2009/0008331 A1 | 1/2009 | Wilt |
| 2009/0010627 A1 | 1/2009 | Lindsay |
| 2009/0076434 A1 | 3/2009 | Mischelevich |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0083331 A1 | 3/2009 | Oh |
| 2009/0095679 A1 | 4/2009 | Demers |
| 2009/0101549 A1* | 4/2009 | Kamen ............ A61M 1/106 210/85 |
| 2009/0101552 A1 | 4/2009 | Fulkerson |
| 2009/0101577 A1 | 4/2009 | Fulkerson |
| 2009/0105627 A1 | 4/2009 | Rohde |
| 2009/0107902 A1 | 4/2009 | Childers |
| 2009/0112507 A1* | 4/2009 | Edney ............ G01N 33/2888 702/136 |
| 2009/0113335 A1 | 4/2009 | Sandoe |
| 2009/0114037 A1 | 5/2009 | Smith |
| 2009/0120864 A1 | 5/2009 | Fulkerson |
| 2009/0124963 A1 | 5/2009 | Hogard |
| 2009/0127193 A1 | 5/2009 | Updyke |
| 2009/0127793 A1 | 5/2009 | Ferris |
| 2009/0137940 A1 | 5/2009 | Orr |
| 2009/0173682 A1 | 7/2009 | Robinson |
| 2009/0282980 A1 | 11/2009 | Gura |
| 2009/0312694 A1 | 12/2009 | Bedingfield |
| 2010/0022936 A1 | 1/2010 | Gura |
| 2010/0078381 A1 | 4/2010 | Merchant |
| 2010/0078387 A1 | 4/2010 | Wong |
| 2010/0084330 A1 | 4/2010 | Wong |
| 2010/0094193 A1 | 4/2010 | Gura |
| 2010/0100034 A1 | 4/2010 | Wich-Heiter |
| 2010/0101664 A1 | 4/2010 | Yamamoto |
| 2010/0116048 A1 | 5/2010 | Fulkerson |
| 2010/0116740 A1 | 5/2010 | Fulkerson |
| 2010/0129247 A1 | 5/2010 | Lauer |
| 2010/0133153 A1 | 6/2010 | Beden |
| 2010/0140149 A1 | 6/2010 | Fulkerson |
| 2010/0179464 A1 | 7/2010 | Smith |
| 2010/0184198 A1 | 7/2010 | Joseph |
| 2010/0192686 A1 | 8/2010 | Kamen |
| 2010/0209300 A1 | 8/2010 | Dirac |
| 2010/0312161 A1 | 12/2010 | Jonsson |
| 2010/0326911 A1 | 12/2010 | Rosenbaum |
| 2010/0326916 A1 | 12/2010 | Wrazel |
| 2011/0000830 A1 | 1/2011 | Ikeda |
| 2011/0000832 A1 | 1/2011 | Kelly |
| 2011/0009799 A1 | 1/2011 | Mullick |
| 2011/0017665 A1 | 1/2011 | Updyke |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani |
| 2011/0054352 A1 | 3/2011 | Ko |
| 2011/0054378 A1 | 3/2011 | Fulkerson |
| 2011/0071465 A1 | 3/2011 | Wang |
| 2011/0083746 A1 | 4/2011 | Hoang |
| 2011/0087187 A1 | 4/2011 | Beck |
| 2011/0092907 A1 | 4/2011 | Krogh |
| 2011/0093294 A1 | 4/2011 | Elahi |
| 2011/0098545 A1 | 4/2011 | Ross |
| 2011/0098624 A1 | 4/2011 | McCotter |
| 2011/0098625 A1 | 4/2011 | Masala |
| 2011/0098635 A1 | 4/2011 | Helmore |
| 2011/0105877 A1 | 5/2011 | Wilt |
| 2011/0105981 A1 | 5/2011 | Wagner |
| 2011/0105983 A1 | 5/2011 | Kelly |
| 2011/0105984 A1 | 5/2011 | Patel |
| 2011/0106002 A1 | 5/2011 | Helmore |
| 2011/0106047 A1 | 5/2011 | Burbank |
| 2011/0106466 A1 | 5/2011 | Furmanski |
| 2011/0107251 A1 | 5/2011 | Guaitoli |
| 2011/0108482 A1 | 5/2011 | Lovell |
| 2011/0125073 A1 | 5/2011 | Rambod |
| 2011/0126714 A1 | 6/2011 | Brugger |
| 2011/0132838 A1 | 6/2011 | Curtis |
| 2011/0132841 A1 | 6/2011 | Rohde |
| 2011/0137224 A1 | 6/2011 | Ibragimov |
| 2011/0137264 A1 | 6/2011 | Chelak |
| 2011/0139704 A1 | 6/2011 | Choi |
| 2011/0140896 A1 | 6/2011 | Menzel |
| 2011/0141116 A1 | 6/2011 | Dalesch |
| 2011/0152739 A1 | 6/2011 | Roncadi |
| 2011/0155657 A1 | 6/2011 | Collins |
| 2011/0160649 A1 | 6/2011 | Pan |
| 2011/0166507 A1 | 7/2011 | Childers |
| 2011/0168614 A1 | 7/2011 | Pouchoulin |
| 2011/0171713 A1 | 7/2011 | Bluchel |
| 2011/0189048 A1 | 8/2011 | Curtis |
| 2011/0208072 A1 | 8/2011 | Pfeiffer |
| 2011/0208106 A1 | 8/2011 | Levin |
| 2011/0213289 A1 | 9/2011 | Toyoda |
| 2011/0218475 A1 | 9/2011 | Brugger |
| 2011/0218487 A1 | 9/2011 | Shang |
| 2011/0226680 A1 | 9/2011 | Jonsson |
| 2011/0230814 A1 | 9/2011 | Kopperschmidt |
| 2011/0232388 A1 | 9/2011 | Butterfield |
| 2011/0237997 A1 | 9/2011 | Beden |
| 2011/0237998 A1 | 9/2011 | Wariar |
| 2011/0240537 A1 | 10/2011 | Ferrarini |
| 2011/0240555 A1 | 10/2011 | Ficheux |
| 2011/0269167 A1 | 11/2011 | Bene |
| 2011/0272337 A1 | 11/2011 | Palmer |
| 2011/0272352 A1 | 11/2011 | Braig |
| 2011/0275984 A1 | 11/2011 | Biewer |
| 2011/0284464 A1 | 11/2011 | Roncadi |
| 2011/0297593 A1 | 12/2011 | Kelly |
| 2011/0297598 A1 | 12/2011 | Lo |
| 2011/0297599 A1 | 12/2011 | Lo |
| 2011/0300010 A1 | 12/2011 | Jamagin |
| 2011/0300230 A1 | 12/2011 | Peterson |
| 2011/0303588 A1 | 12/2011 | Kelly |
| 2011/0303590 A1 | 12/2011 | Childers |
| 2011/0303598 A1 | 12/2011 | Lo |
| 2011/0309019 A1 | 12/2011 | Ahrens |
| 2011/0315611 A1 | 12/2011 | Fulkerson |
| 2012/0010554 A1 | 1/2012 | Vantard |
| 2012/0018377 A1 | 1/2012 | Tsukamoto |
| 2012/0018378 A1 | 1/2012 | Kelly |
| 2012/0022440 A1 | 1/2012 | Childers |
| 2012/0029324 A1 | 2/2012 | Akonur |

(56) References Cited

U.S. PATENT DOCUMENTS

| | | |
|---|---|---|
| 2012/0029937 A1 | 2/2012 | Neftel |
| 2012/0031826 A1 | 2/2012 | Childers |
| 2012/0035534 A1 | 2/2012 | Yu |
| 2012/0037550 A1 | 2/2012 | Childers |
| 2012/0043279 A1 | 2/2012 | Kelly |
| 2012/0065567 A1 | 3/2012 | Zarate |
| 2012/0075266 A1 | 3/2012 | Shimizu |
| 2012/0214117 A1 | 8/2012 | Broker |
| 2013/0140652 A1 | 6/2013 | Erdler |
| 2013/0199998 A1 | 8/2013 | Kelly |
| 2013/0220907 A1 | 8/2013 | Fulkerson |
| 2014/0199193 A1 | 7/2014 | Wilt |

FOREIGN PATENT DOCUMENTS

| | | |
|---|---|---|
| CN | 101311589 | 11/2008 |
| EP | 0808633 | 11/1997 |
| EP | 2237814 | 10/2010 |
| JP | S56138580 U | 10/1981 |
| JP | S5755010 U | 3/1982 |
| JP | S5913770 U | 1/1984 |
| JP | S59127978 U | 8/1984 |
| JP | S6037674 U | 3/1985 |
| JP | S60108870 | 6/1985 |
| JP | S60108870 U | 7/1985 |
| JP | H02114269 U | 9/1990 |
| JP | H0413143 U | 2/1992 |
| JP | H05172268 A | 9/1993 |
| JP | 2002119585 A | 4/2002 |
| JP | 2002139165 A | 5/2002 |
| JP | 2002523772 | 7/2002 |
| JP | 2003502091 | 1/2003 |
| JP | 2004057284 | 2/2004 |
| JP | 2008291911 A | 4/2008 |
| JP | 2008531192 | 8/2008 |
| JP | 2008531192 A1 | 8/2008 |
| JP | 2009521965 | 6/2009 |
| MX | 20103880 | 7/2010 |
| WO | 8002806 | 12/1980 |
| WO | 9625214 | 8/1996 |
| WO | 9727490 | 7/1997 |
| WO | 9823353 | 6/1998 |
| WO | 2005089832 A2 | 9/2005 |
| WO | 2006009362 | 9/2006 |
| WO | 2006120415 | 11/2006 |
| WO | 2007028056 | 3/2007 |
| WO | 2009045589 A2 | 4/2009 |
| WO | 2009073567 | 6/2009 |
| WO | 2009091963 | 7/2009 |
| WO | 2009157877 | 12/2009 |
| WO | 2010042666 | 4/2010 |
| WO | 2010042667 | 4/2010 |
| WO | 2010062698 | 6/2010 |
| WO | 2010081121 | 7/2010 |
| WO | 2010114932 | 10/2010 |
| WO | 2012108910 | 8/2012 |
| WO | 2014105267 A1 | 7/2014 |
| WO | 2014105755 | 7/2014 |
| WO | 2015069412 A1 | 5/2015 |

OTHER PUBLICATIONS

Notice of Allowance dated Dec. 1, 2015 for U.S. Appl. No. 13/852,918.
First Office Action for PA11004600, Aug. 15, 2014.
International Preliminary Report on Patentability for PCT/US13/77234, Jun. 30, 2015.
Notice of Allowance dated Nov. 17, 2015 for U.S. Appl. No. 13/372,202.
Office Action dated Jul. 16, 2015 for U.S. Appl. No. 14/077,112.
International Search Report for PCT/US14/60122, Jan. 21, 2015.
Notice of Allowance dated Feb. 8, 2016 for U.S. Appl. No. 13/726,457.
Second Office Action for Canadian Application No. CA2706919, dated Oct. 27, 2015.
Office Action for Canadian Patent Application No. CA2739807, Oct. 28, 2015.
First Office Action for Canadian Patent Application No. CA2739786, Oct. 21, 2015.
Third Office Action for CN2010800039317, Sep. 10, 2014.
Notice of Allowance dated Feb. 5, 2016 for U.S. Appl. No. 13/548,711.
Notice of Allowance dated Feb. 1, 2016 for U.S. Appl. No. 13/337,227.
Notice of Allowance dated Dec. 28, 2015 for U.S. Appl. No. 14/077,112.
First Examination Report for New Zealand Patent Application No. 614053, Jun. 9, 2014.
First Examination Report for New Zealand Patent Application No. 627386, Aug. 4, 2015.
First Examination Report for New Zealand Patent Application No. 627392, Aug. 4, 2015.
Patent Examination Report No. 1 for Australian Patent Application No. AU2014262300, Sep. 11, 2015.
First Office Action for Japanese Patent Application No. JP2014203093, Nov. 10, 2015.
First Examination Report for New Zealand Patent Application No. 627399, dated Nov. 9, 2015.
First Office Action for Japanese Patent Application No. JP2013553422, dated Sep. 1, 2015.
Office Action dated Mar. 11, 2016 for U.S. Appl. No. 14/040,362.
Notice of Allowance dated Aug. 3, 2016 for U.S. Appl. No. 14/040,362.
Office Action dated Jan. 27, 2015 for U.S. Appl. No. 13/372,202.
Notice of Allowance dated Jun. 9, 2015 for U.S. Appl. No. 13/726,450.
Office Action dated Apr. 17, 2015 for U.S. Appl. No. 13/726,457.
Office Action dated Feb. 12, 2015 for U.S. Appl. No. 13/548,711.
Office Action dated Jan. 15, 2015 for U.S. Appl. No. 13/726,450.
Office Action dated Jul. 1, 2015 for U.S. Appl. No. 13/852,918.
Office Action dated Jul. 15, 2014 for U.S. Appl. No. 13/548,711.
Office Action dated Mar. 4, 2015 for U.S. Appl. No. 13/337,227.
Office Action dated Mar. 7, 2014 for U.S. Appl. No. 13/548,711.
Office Action dated Sep. 17, 2015 for U.S. Appl. No. 13/548,711.
Office Action dated Sep. 3, 2015 for U.S. Appl. No. 13/726,457.
Office Action dated Aug. 27, 2015 for U.S. Appl. No. 13/337,227.
Notice of Allowance dated Jul. 27, 2015 for U.S. Appl. No. 12/751,390.
Examination Report for Mexican Patent Application No. MX/a/2015/004503, Aug. 8, 2016.
Timby et al., Introductory Medical-Surgical Nursing, Lippincott Williams Wilkins, Ninth Edition, Chapter 28, p. 433.
Anthony J. Wing et al., 'Dialysate Regeneration', Replacement of Renal Function by Dialysis, Chapter 17, 323-340 (William Drukker et al., eds., Martinus Nijhoff Publishers, 2nd ed., 1983).
CD Medical, Inc., 'Operator's Manual Drake Willock 480 Ultrafiltration Control Single Patient Delivery System', 1988.
Cobe Laboratories, Inc., 'CentrySystem 3 Dialysis Control Unit Operators Manual', Sep. 1988.
Fresenius AG, 'Acumen Acute Dialysis Machine Operating Instructions', Version 1.0, May 1996.
International Preliminary Report on Patentability for PCT/US2009/059907, Apr. 15, 2010, Fresenius Medical Care Holdings, Inc.
International Search Report for PCT/US09/59907, Xcorporeal, Inc., Apr. 13, 2010.
Manns et al., 'The acu-men: A New Device for Continuous Renal Replacement Therapy in Acute Renal Failure', Kidney International, vol. 54 (1998), 268-274.
NxStage Medical, Inc., 'NxStage System One User's Guide', Software Version 4.3, Part 1 through Part 6-20, 2006.
NxStage Medical, Inc., 'NxStage System One User's Guide', Software Version 4.3, Part 6-20 through Part C-17, 2006.
REDY 2000 Operator's Manual (1991) (Sorbent cartridge-based hemodialysis system).
REDY 2000 Service Manual (1989) (Sorbent cartridge-based hemodialysis system).

(56) References Cited

OTHER PUBLICATIONS

Renal Solutions, Inc., 'Dialysate Tubing Set and Dialysate Reservoir Bag for the Allient Sorbent Hemodialysis System', Instructions, 2004.
Renal Solutions, Inc., 510(K) for the SORB+ and HISORB+ Cartridges, Mar. 31, 2003.
Renal Solutions, Portions of the Allient Sorbent Hemodialysis System, Home User Manual, 2006, Chapters 1-3.
Reyes et al., 'Acid-Base Derangements During Sorbent Regenerative Hemodialysis in Mechanically Ventilated Patients', Critical Care Medicine, vol. 19, No. 4, 1991, 554-559 (col. 2, lines 17-22).
Seratron Dialysis Control System Operations Manual (cumulative 1980).
Ward et al., 'Sorbent Dialysis Regenerated Dialysis Delivery Systems', Peritoneal Dialysis Bulletin, Chapter 8, 3(2): S41-S48 (Apr.-Jun. 1983).
COBE Renal Care, Inc., "Sorbent Dialysis Primer", Edition 4, Sep. 1993.
Examination Report for PCT/US08/85062, Mexican Patent Office, Mar. 11, 2013.
Examination Report for PCT/US09/59906, New Zealand Intellectual Property Office, May 15, 2012.
Fresenius USA, Inc., "Fresenius 2008H Hemodialysis Machine", Part No. 490005, Revision H, 1994-2001.
International Search Report for PCT/US09/31228, Xcorporeal, Inc., Jun. 19, 2009.
International Search Report for PCT/US09/59906, Xcorporeal, Inc., May 8, 2012.
International Search Report for PCT/US09/62840, Xcorporeal, Inc. Feb. 10, 2012.
International Search Report for PCT/US10/20698, Xcorporeal, Inc., Jun. 16, 2010.
International Search Report for PCT/US10/29500, Xcorporeal, Inc., Jul. 2, 2010.
International Search Report for PCT/US11/53184, Xcorporeal, Inc., Mar. 2, 2012.
International Search Report for PCT/US13/77234, Jun. 9, 2014.
International Search Report PCT/US08/85062, Mar. 20, 2009, XCorporeal, Inc.
Renal Solutions, Inc., Portions of 510(k) Allient Sorbent Hemodialysis System (Allient Main Controller Software Architecture Overview), Renal Solutions, Inc., Dec. 17, 2004.
Renal Solutions, Inc., Portions of 510(k) Allient Sorbent Hemodialysis System (Sections A-I), Dec. 17, 2004.
Renal Solutions, Inc., Portions of 510(k) Allient Sorbent Hemodialysis System (Sections M.3 and M.4), Renal Solutions, Inc., Dec. 17, 2004.
Renal Solutions, Portions of the Allient Sorbent Hemodialysis System, Home User Manual, 2006, Chapters 4.
Renal Solutions, Portions of the Allient Sorbent Hemodialysis System, Home User Manual, 2006, Chapters 5 to end.
Renal Solutions, Portions of the Allient Sorbent Hemodialysis System, Operator Manual, 2008, Chapter 3.
Renal Solutions, Portions of the Allient Sorbent Hemodialysis System, Operator Manual, 2008, Chapter 4, 4-1 to 4-33.
Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
Renal Solutions, Portions of the Allient Sorbent Hemodialysis System, Operator Manual, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual Model 1500, 2008, Chapter 3, 3-31 to 3-70.
Renal Solutions, Portions of the Allient Sorbent Hemodialysis System, Operator Manual Model 1500, 2008, Chapters 1 to 2.
Renal Solutions, Special 510(k) Device Modification, Allient Sorbent Hemodialysis System, Mar. 15, 2007.
Extended European Search Report for Application No. EP10729646.9, dated Jul. 23, 2015.
European Search Report for Application No. EP20090829649, dated Jan. 22, 2015.
First Office Action for Canadian Application No. CA2706919, dated Jan. 20, 2015.
First office action for Chinese Patent Application No. CN201180069761, Jan. 21, 2015.
International Search Report for PCT/US2013/068506, Apr. 9, 2014.
Notice of Allowance dated Apr. 13, 2016 for U.S. Appl. No. 14/291,448.

\* cited by examiner

400

MODULAR RESERVOIR ASSEMBLY FOR A HEMODIALYSIS AND HEMOFILTRATION SYSTEM

CROSS-REFERENCE

The present invention relies on U.S. Patent Provisional No. 61/165,389, filed on Mar. 31, 2009, for priority. The present invention is also a continuation-in-part of U.S. patent application Ser. No. 12/610,032, filed on Oct. 30, 2009, which relies on U.S. Provisional Application No. 61/109,834, filed on Oct. 30, 2008. The present invention is also related to a) U.S. patent application Ser. No. 12/575,450, filed on Oct. 7, 2009, b) U.S. patent application Ser. No. 12/575,449, filed on Oct. 7, 2009, c) U.S. patent application Ser. No. 12/355,102, filed on Jan. 16, 2009, d) U.S. patent application Ser. No. 12/355,128, filed on Jan. 16, 2009, e) U.S. patent application Ser. No. 12/351,969, filed on Jan. 12, 2009, f) U.S. patent application Ser. No. 12/324,924, filed on Nov. 28, 2008, g) U.S. patent application Ser. No. 12/210,080, filed on Sep. 12, 2008, h) U.S. patent application Ser. No. 12/238,055, filed on Sep. 25, 2008, i) U.S. patent application Ser. No. 12/237,914, filed on Sep. 25, 2008, j) U.S. patent application Ser. No. 12/249,090, filed on Oct. 10, 2008, k) U.S. patent application Ser. No. 12/245,397, filed on Oct. 3, 2008, l) U.S. patent application Ser. No. 12/610,100, filed on Oct. 30, 2009, and m) U.S. Pat. No. 12/705,054, filed on Feb. 12, 2010. All of the aforementioned applications are herein incorporated by reference.

FIELD OF THE INVENTION

The present invention generally relates to the field of dialysis and more specifically to a portable dialysis system with a modular reservoir assembly, capable of conducting hemodialysis and hemofiltration.

BACKGROUND OF THE INVENTION

Hemodialysis is used for removing toxic wastes from the human body in cases of renal failure, and involves using an artificial kidney in conjunction with an associated machine. The patient's blood is temporarily brought outside of the body with the help of tubes and passed through at least one semipermeable membrane, which may be a group of hollow fibers, in the artificial kidney, also called a dialyzer. The semi permeable membrane separates the blood from dialysate solution. The impurities from the blood pass through the membrane and into the dialysate solutions primarily by osmotic pressures. The cleansed blood is then returned to the body. During this procedure, it may also be necessary to remove excess fluids from the body. This is accomplished by a process known as hemofiltration or ultrafiltration. In this process, I.V. quality, or sterile, replacement fluid is infused into the patient by a direct connection between the dialysate circuit and the blood circuit (by-passing the dialyzer) and an equal amount of fluid is removed from the patient by taking the fluid off through the dialyzer and discarding it. Further, an additional amount of fluid in the form of ultrafiltrate may be optionally removed to obtain a net removal of fluid from a fluid-overloaded patient. The amount of ultrafiltrate removed from the patient is normally controlled by pressure across the semipermeable membrane. This transmembrane pressure is the result of the differential between the blood pressure and the pressure which exists on the dialysate side of the membrane.

Hemodialysis procedures using standard equipment tend to be cumbersome as well as costly, in addition to requiring the patient to be bound to a dialysis center for long durations. Conventional systems are also less reliable because of the necessity of using myriad of tubes comprising the fluid circuits of the purification systems, thus increasing the risks of leakage and breakage. Besides being difficult to transport due to their large size, conventional hemodialysis machines also suffer from a lack of flexibility. For example, sorbent based hemodialysis procedures have a particular set of hardware requirements that are not shared by the hemofiltration process. Thus, it would be beneficial to have common hardware components such as the pumping system, which can be used such that the dialysis system can be operated in hemofiltration as well as hemodialysis modes.

Additionally, there is a need for a portable system that can effectively provide the functionality of a dialysis system in a safe, cost-effective, and reliable manner. In particular, there is a need for a compact dialysis fluid reservoir system that can satisfy the fluid delivery requirements of a dialysis procedure while integrating therein various other critical functions, such as fluid heating, fluid measurement and monitoring, and leak detection.

SUMMARY OF THE INVENTION

The present invention is direct toward multiple embodiments. In one embodiment, the present application discloses a dialysis system having a reservoir module comprising a reservoir housing having four sides, a base, and a top, wherein said four sides, base surface, and top surface define an internal space; a surface located within said internal space for supporting a container adapted to contain dialysate; and a conductivity sensor located within said internal space, wherein said conductivity sensor comprises a coil having a plurality of turns, a capacitor in electrical communication with said coil, wherein said coil and capacitor define a circuit, and an energy source in electrical communication with said circuit.

Optionally, the energy source maintains a substantially constant voltage across said capacitor. Optionally, the conductivity sensor outputs a value indicative of a sodium concentration in said dialysate based on an energy input required from said energy source to maintain the constant voltage across the capacitor. Optionally, the coil has a radius between 2 and 6 inches. Optionally, the coil generates a magnetic field. Optionally, the surface is a flat pan. Optionally, a heater is in thermal contact with said pan. Optionally, the heater is integrated into said pan. Optionally, the surface is part of a scale, which comprises a plurality of flex points physically attached to said top. Optionally, the container is a disposable or reusable bag. Optionally, the reservoir housing further comprises a gutter which is in fluid communication with a wetness sensor. Optionally, the door providing internal access to said reservoir housing is integrated into one of said four sides.

In another embodiment, the present specification discloses a module for use in an extracorporeal system comprising a housing having four sides, a base, and a top, wherein said four sides, base surface, and top surface define an internal space; a container positioned within said internal space and adapted to contain a liquid; and a conductivity sensor located within said internal space, wherein said conductivity sensor comprises a coil having a plurality of turns, a capacitor in electrical communication with said coil, wherein said coil and capacitor define a circuit, and an energy source in electrical communication with said circuit.

Optionally, the conductivity sensor outputs a value indicative of an ion concentration, such as a sodium ion, in the liquid based on an energy input required from said energy source to maintain a constant voltage across the capacitor. Optionally, the coil has a radius between 2 and 6 inches. Optionally, the energy source is adapted to maintain a substantially constant voltage across said capacitor. Optionally, the conductivity sensor further comprises an oscillator. Optionally, the conductivity sensor further comprises automatic gain control.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

Figure 1:
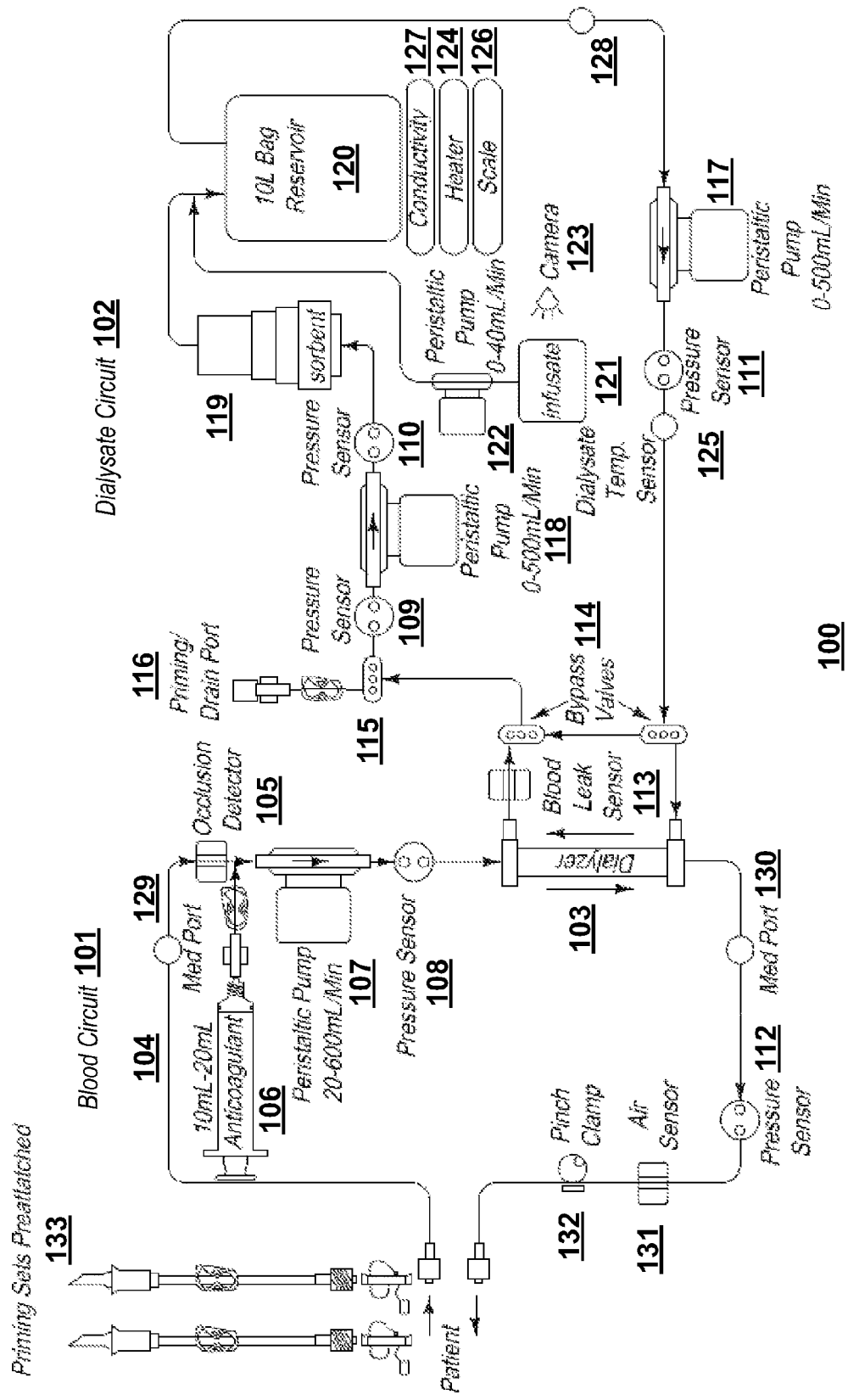
FIG. 1 shows the fluidic circuit for an extracorporeal blood processing system.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention is directed towards a dialysis unit that is modular and portable, and capable of operating with hemodialysis as well as hemofiltration protocols. In one embodiment, one of the main functional modules of the modularized dialysis system is built around the dialysate reservoir and integrates the reservoir with the reservoir weighing system, heater, and various sensors.

FIG. 1 shows the fluidic circuit for an extracorporeal blood processing system 100, used for conducting hemodialysis and hemofiltration. The hemodialysis system comprises two circuits—a Blood Circuit 101 and a Dialysate Circuit 102. Blood treatment during dialysis involves extracorporeal circulation of blood through an exchanger having a semi permeable membrane, the hemodialyser or dialyzer 103. The patient's blood is circulated in the blood circuit 101 on one side of the membrane (dialyzer) 103 and a dialysis liquid called the dialysate, comprising required blood electrolytes in sufficient concentrations, is circulated on the other side in the dialysate circuit 102. The circulation of dialysate fluid thus provides for the regulation of the electrolytic concentration in blood.

The patient line 104, which feeds blood to the dialyzer 103 in the blood circuit 101, is provided with an occlusion detector 105 which is generally linked to a visual or audible alarm (not shown) to signal any obstruction to the blood flow. In order to prevent coagulation of blood, a syringe, injector, input, or other means 106 for injecting an anticoagulant, such as heparin, into the blood is also provided. A peristaltic pump 107 is also provided to ensure flow of blood in the normal (desired) direction and a port 129 for inserting, injecting, or otherwise inputting into the blood stream medicines is also provided upstream from the pump. Another medical port 130 is provided before clean blood from the dialyzer is returned to the patient. An AIL sensor 131 and a pinch clamp 132 are employed in the circuit to ensure a smooth and unobstructed flow of clean blood to the patient. Priming sets 133 are pre-attached to the hemodialysis system and help prepare the system before it is used for dialysis.

A pressure sensor 108 is provided at the inlet where blood enters the dialyzer 103. Other pressure sensors 109, 110, 111 and 112 are provided at various positions in the hemodialysis system that help keep track of and maintain fluid pressure at vantage points.

At the point where used dialysate fluid from the dialyzer 103 enters the dialysate circuit 102, a blood leak sensor 113 is provided to sense and prevent any leakage of blood into the dialysate circuit. Bypass valves 114 are also provided at the dialyzer 103 input and output endpoints of the dialysate circuit, which ensure that fluid flow is in the desired direction in the closed loop circuit. Another bypass valve 115 is provided just before a priming/drain port 116. The port 116 is used for initially preparing the circuit curves with a priming solution, and to remove used dialysate fluid during dialysis and replace portions of dialysate with replenishment fluid of appropriate sodium concentration so that overall sodium concentration of the dialysate is maintained at a desired level.

The dialysate circuit is provided with two peristaltic pumps 117 and 118. Pump 117 is used for pumping out used dialysate fluid to the drain or waste container, as well as for pumping regenerated dialysate into the dialyzer 103. Pump 118 is used for pumping out spent dialysate from the dialyzer 103, and also for pumping in the replacement fluid from port 116 for maintaining sodium concentration in the dialysate.

A sorbent type cartridge 119 is provided in the dialysate circuit, which contains several layers of materials, each having a specific role in removing impurities such as urea. The combination of these materials allows water suitable for drinking to be charged into the system for use as dialysate fluid. That is, the sorbent cartridge enables regeneration of fresh dialysate from the spent dialysate coming from the dialyzer. For the fresh dialysate fluid, a lined container or reservoir 120 of a suitable capacity such as 5, 8 or 10 liters is provided. In one embodiment, the reservoir is in the form of a disposable bag.

Depending upon patient requirement, desired quantities of an infusate solution 121 may be added to the dialysis fluid. Infusate 121 is a sterile solution containing minerals and/or glucose that help maintain minerals like potassium and calcium in the dialysate fluid at levels similar to their natural concentration in healthy blood. A peristaltic pump 122 is provided to pump the desired amount of infusate solution to the container 120 and thereby mix with cleansed, recycled dialysate solution. A camera or other sensor 123 may optionally be provided to monitor the flow of the infusate solution.

A heater 124 is provided to maintain the temperature of dialysate fluid in the container 120 at the required level. The temperature of the dialysate fluid can be sensed by the temperature sensor 125. The container 120 is also equipped with a scale 126 for keeping track of the weight of the fluid in the container and a conductivity meter 127, which displays the conductivity of the dialysate fluid measured by the conductivity sensor 128. The conductivity sensor 128 provides an indication of the level of sodium in the dialysate. In one embodiment, the conductivity sensor 128 is a non-contact type of sensor. Further, the container 120 is also equipped with an ammonia sensor (not shown) to keep track of ammonia levels and to signal if ammonia breakthrough occurs.

It should be appreciated that the aforementioned fluid circuits, and associated components, can be implemented in a variety of configurations. A preferred configuration is disclosed in U.S. patent application Ser. No. 12/610,032, filed on Oct. 30, 2009, which is a parent application to the present specification, and Ser. No. 12/324/924, filed on Nov. 28, 2008. As disclosed in those applications, the fluid circuits are preferably embodied in a portable system that comprises compact functional modules, each of which is small, detachable, and easily transported.

Figure 2:
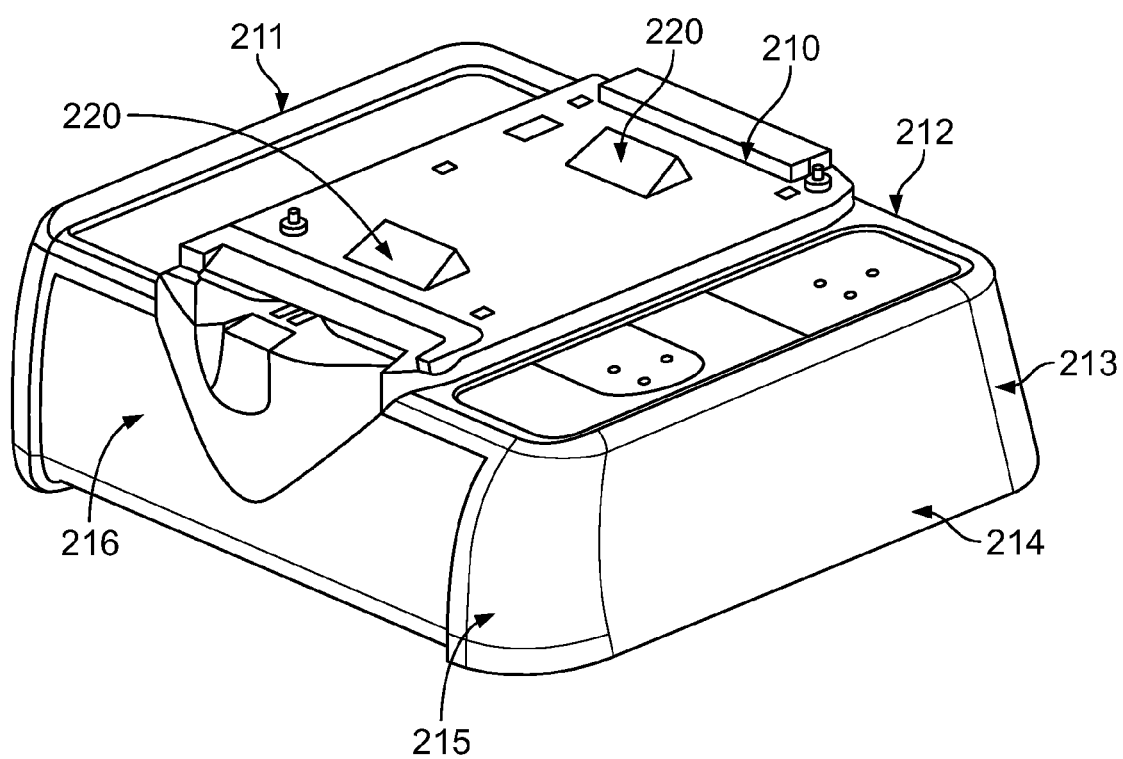
FIG. 2 schematically illustrates the reservoir assembly module, according to one embodiment of the present invention.

In one embodiment, the main components of the reservoir section of the dialysate circuit, such as the reservoir bag 120, conductivity sensor 127, heater 124, and scale 126, are integrated in a single housing. FIG. 2 illustrates a schematic figure for the reservoir assembly module 200 of the modular hemodialysis/hemofiltration system, according to one embodiment of the present invention. The reservoir module 200 is a substantially rectangular housing having a right side 213, left side 211, base surface 214, top surface 210, back side 212, and front side 215 with a door 216 to access the internal space defined by the housing walls. The reservoir module preferably functions as the base structure in a portable dialysis system and comprises receiving structures 220 that receive a top unit which functions as the dialysis controller unit and comprises manifolds with the fluidic circuitry. In one embodiment, the reservoir module 200 also comprises an input/output through which fluidic access can be established between the fluidic circuits in the top unit and the reservoir bag and fluid contained within the reservoir module 200.

The reservoir module 200 built around the dialysate reservoir has a number of components incorporated that are related both to the reservoir as well as specifically to sorbent dialysis. Since FIG. 2 provides only an outside view of the reservoir subsystem module, the various components integrated inside the module are not visible. These components are illustrated in greater detail in FIGS. 3 and 4.

In one embodiment, components of the reservoir subsystem assembly include, but are not limited to a dialysate reservoir, including disposable reservoir liner or bag, dialysate heater, dialysate temperature monitor, reservoir weighing system, including magnetic flexers and tilt sensor, dialysate ammonia concentration and pH sensor, including disposable sensor elements and reusable optical reader, dialysate conductivity sensor (non contact type), and wetness or leak sensors.

One of ordinary skill in the art would appreciate that apart from the sensors listed above other components in the dialysate circuit, such as pumps and sensors such as pressure transducers may also be included within the reservoir module. Further, various sensors such as ammonia and pH sensors may be integrated as individual sensors into the reservoir module, or as a single 'sensor sub-module' that comprises all the sensors.

The inclusion of each of these components is designed in a manner that makes the reservoir assembly module specially suited for use in the operation of a recirculating sorbent based dialysis system. Further, the module is also designed such that during other forms of dialysis, such as single pass hemofiltration, any unnecessary elements of the module that are specific only to sorbent based dialysis, can be removed.

Figure 3:
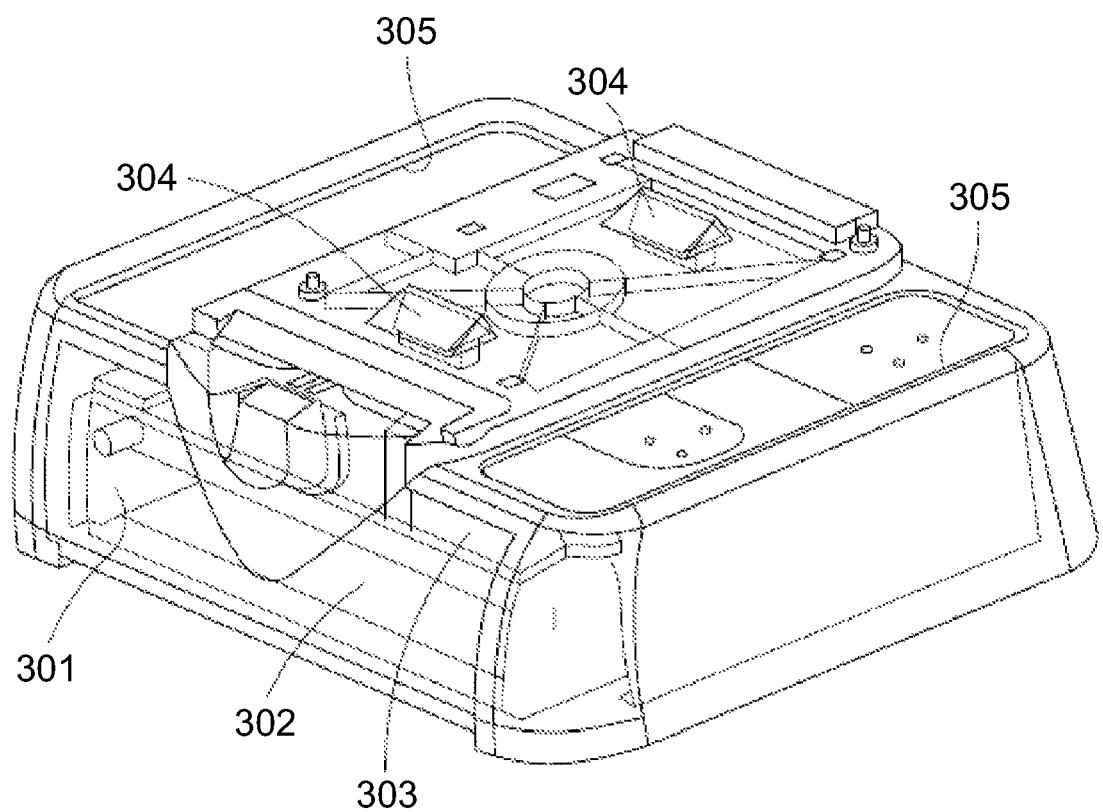
FIG. 3 provides a perspective view of the reservoir assembly module with the outer cover rendered transparent to show the internal arrangement.
Figure 4:
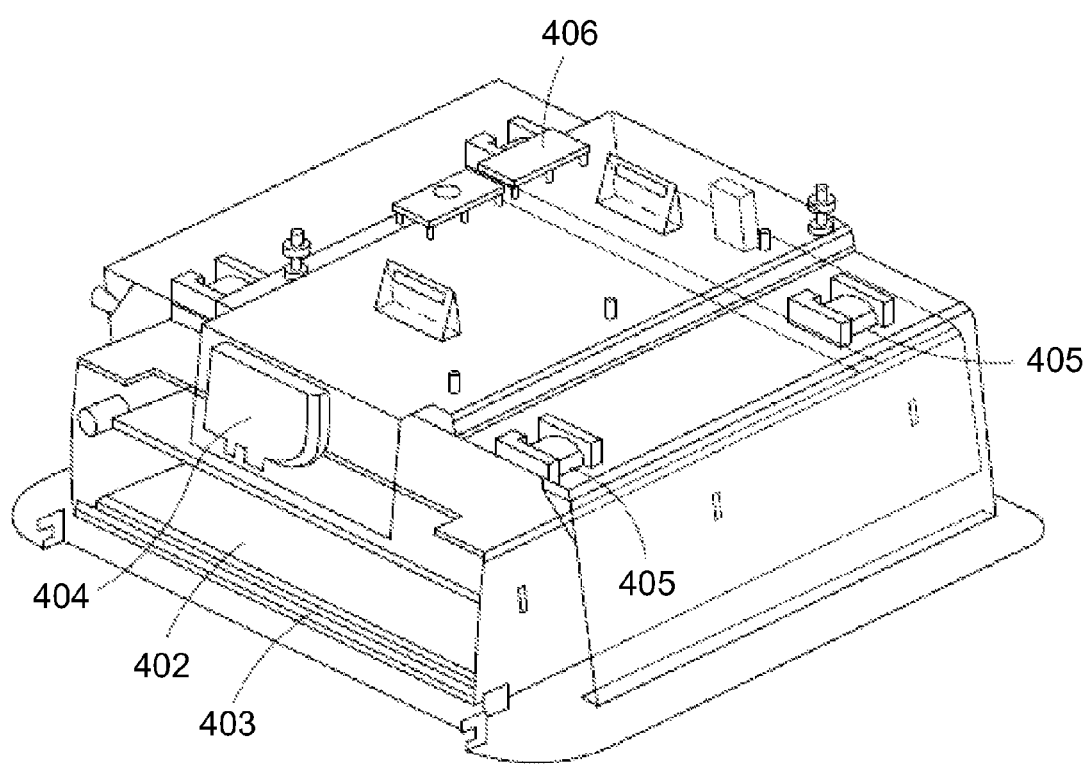
FIG. 4 illustrates another view of the reservoir assembly module, according to one embodiment of the present invention.

Details of the reservoir assembly module are shown in FIGS. 3 and 4. FIG. 3 illustrates one embodiment of the reservoir assembly module, with the outer skins or covers rendered transparent, thereby revealing the internal arrangement. Referring to FIG. 3, an opening 301 is provided in the front of the reservoir subsystem module 300. The main function of the reservoir subassembly is containment of the dialysate. The opening 301 allows a disposable reservoir bag, which can be a conventional IV bag with dialysate contained therein, to be inserted. The reservoir module 300 is also provided with a pan 302 inside the front opening for containing the reservoir bag. In one embodiment, a flat film heater and temperature sensor (not shown) are both located underneath the bottom of the reservoir pan 302, and help maintain the temperature of dialysate fluid at body temperature or close to it. In one embodiment, the temperature of the dialysate fluid can be set by the user.

In one embodiment, the reservoir pan 302 is suspended in a scale mechanism 303. The scale mechanism 303 can be used for accurate measurement of the weight of the dialysate'fluid in the reservoir bag prior to start of the dialysis, and for maintaining volumetric balance of the dialysate fluid in the circuit during dialysis.

On the top of reservoir assembly module 300, features 304 for attachment to the pumping unit of the dialysis system are provided. These features help in easy coupling and removal of the reservoir assembly module from the pumping unit, which in one embodiment may be mounted on the top of the reservoir assembly. The top of the reservoir assembly module is also equipped with drain gutters 305 on either side of the module. Individual wetness sensors (not shown) are provided in each of the gutters. As known in the art, wetness sensors are optical devices that sense moisture on account of increased coupling of light into fluid as opposed to air, by virtue of the difference of index of refraction between air and fluid. The wetness sensors in the drain gutters 305 keep track of moisture and indicate any leaks in the pumping system when it is mounted on top of the reservoir assembly. By having a separate wetness sensor in the drain gutter on either side, leaks can be localized and specific guidance given to the user regarding any corrections that may be required.

FIG. 4 illustrates another view of the reservoir assembly module, wherein the outer covers of the module 400 are totally removed and some internal components rendered transparent. Referring to FIG. 4, the reservoir pan 402 is provided with an internal gutter 403. The gutter 403 is further equipped with a wetness sensor, which is located just under the dialysate pan 402 so that it can sense a leak inside the reservoir assembly.

The reservoir assembly module 400 further comprises a sensor pod 404 or sub-module, which comprises a collection of various sensors on the same circuit board. The sensor board comprises sensors specifically related to sorbent based dialysis, such as ammonia and pH sensors. In one embodiment, the ammonia sensor comprises of disposable color sensitive strips, which are made up of a material that exhibits a visible change in color in response to the level of ammonia present in the dialysate. For example, the color of the indicator strip may change gradually from blue to yellow, depending on the ammonia level present around that strip. Such visual color indication makes it easier to keep track of ammonia levels and to identify if ammonia breakthrough occurs. In one embodiment, for a more precise assessment of color change in ammonia indicator strips, an optical sensor is used. The optical sensor is also located in the sensor module 404, and can be used for converting the general visible color reading into an accurate indication of ammonia level.

With respect to the dialysate sodium concentration, it should be appreciated that, to perform kidney dialysis properly and cause correct diffusion across the dialyzer, the concentration of sodium must be maintained within a certain range. A conventional method of determining the sodium concentration of a fluid is to measure the fluid's electrical conductivity and the fluid's temperature and then calculate the approximate sodium concentration. An improved method and system for measuring sodium concentration in dialysate in a non-contact manner uses a non contact conductivity sensor built in to the bottom of the reservoir pan 402.

In one embodiment, the non contact conductivity sensor is an inductive device utilizing a coil. Change in sodium concentration changes the conductivity of the dialysate solution, which in turn changes the impedance of the coil. By placing the conductivity sensor in the bottom of the reservoir pan 402, and thus under the dialysate bag in the reservoir, a large surface area is presented to the coil. This ensures high accuracy of measurement, in addition to requiring no physical contact of the sensor with the dialysate fluid.

Figure 8A:
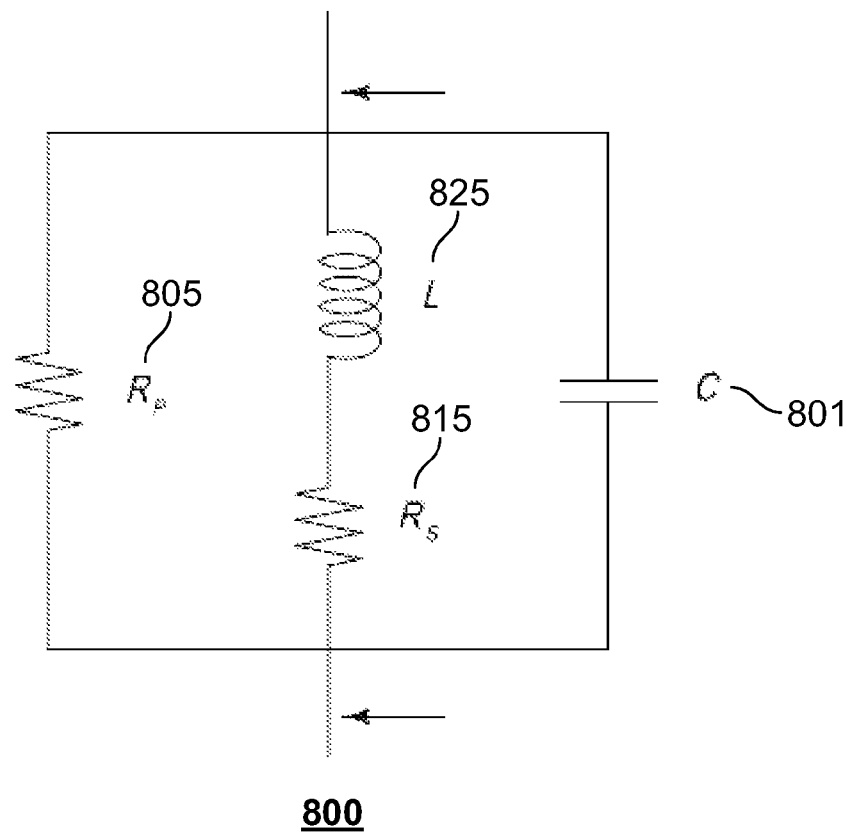
FIG. 8a is a schematic diagram of a resonant circuit used in an exemplary non-contact conductivity sensor.
Figure 8B:
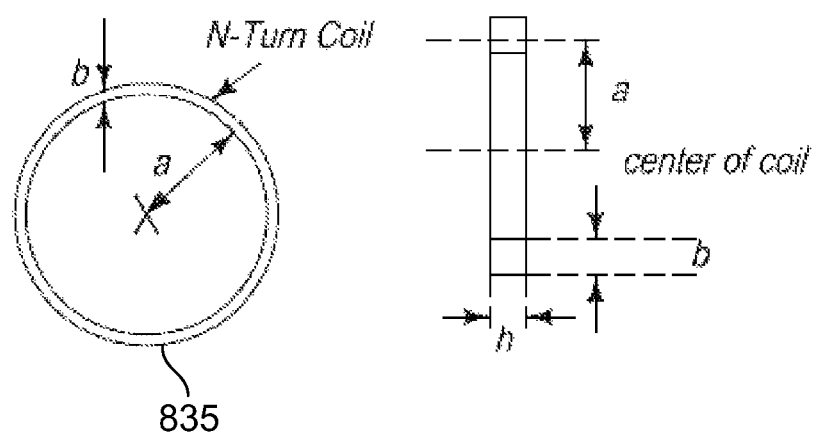
FIG. 8b is a diagram of a coil used in an exemplary non-contact conductivity sensor.

Referring to FIGS. 8a and 8b, components of a non contact electrical conductivity sensor are shown, including a coil 835 with n-turns defining the generation of a magnetic field when properly energized and a diagram of the resulting resonant LCR tank circuit 800 created when the coil, defined by resistance elements Rs 815 and Rp 805 and inductor element L 825, is electrically coupled with a capacitator 801.

The coil 935 is a multi-layer, circular, flat coil used as an energy storage device in conjunction with a capacitor 801. The coil 835 has loss elements, which comprises the electrical resistance of the coil wire Rs 815 and a magnetic field loss element Rp 805, the electrical conductivity of the fluid in the bag.

The coil 835 diameter is a function of magnetic field penetration into the fluid. Another factor for fluid penetration is operating frequency. Low operating frequency will penetrate deeper into the fluid, but with a cost of lower losses. A larger coil will have small effect cause by dimensional tolerances. A defining equation is provided below:

$$L = \frac{0.31(aN)^2}{6a + 9h + 10b}(\mu H)$$

Where a=average radius of the coil in centimeters, N=number of turns, b=winding thickness in centimeters, h=winding height in centimeters. In one embodiment, the radius of the coil is in the range of 2 to 6 inches and, more particularly, 2, 3, 4, 5, and 6 inches and all increments in between.

Referring to the circuit 800, the physical coil 835 is represented by L 825 and Rs 815, with L being the inductance of the coil and Rs being the electrical resistance of the coil wire. Energy loss of the magnetic field produced by L 825 is represented by Rp 805. Energy loss Rp arises from, and is directly related to, the conductivity fluid which is proximate to the coil 835. Therefore, if the coil 835 is placed in the reservoir pan, integrated into the surface of the reservoir pan, or otherwise placed at a distance such that the magnetic field generated by the coil can be affected by the presence of dialysate within a bag, or, more particularly, the conductivity of the dialysate within a bag, changes in bag's sodium concentration, and therefore conductivity, can be monitored and measured by tracking the corresponding changes to the magnetic field generated by the coil 835.

Circuit 800 enables the accurate measurement of changes in the magnetic field generated by the coil 835. When the circuit 800 is driven at its resonant frequency, energy is transferred back and forth between inductive element L 825 and capacitor 801. At resonance, energy losses are proportional to the $I^2R$ losses of $R_S$ and $R_P$. To maintain a constant AC voltage across C 801, energy must be supplied to the circuit 800 and the supplied energy must equal to the energy loss of $R_P$ 805 and $R_S$ 815. When the L 825 and C 801 elements are placed in a Pierce oscillator with automatic gain control, the control voltage will be proportional to the electrical conductivity of the fluid being sensed, since the oscillator will require more energy to oscillate with higher resistive field losses due primarily to changes in dialysate conductivity arising from changes in sodium concentration levels.

As mentioned previously with reference to FIG. 3, the reservoir pan is suspended in a scale mechanism for accurate measurement of the weight and for maintaining volumetric balance of the dialysate fluid in the circuit during dialysis. The suspension points 405 for the scale mechanism are illustrated in FIG. 4. In one embodiment, four suspension points 405 are provided, each of which includes a weighing mechanism. In addition to the four suspension points 405, the reservoir assembly subsystem 400 also includes a level sensor (not shown in FIG. 4). The level sensor allows for computation of accurate weight even if the reservoir bag is not level. FIG. 4 also illustrates pins 406 on the top of the reservoir assembly module 400, which can be used to provide electrical connection to a control and/or pumping unit which, as mentioned earlier, may be mounted on the top of the reservoir assembly.

Figure 5:
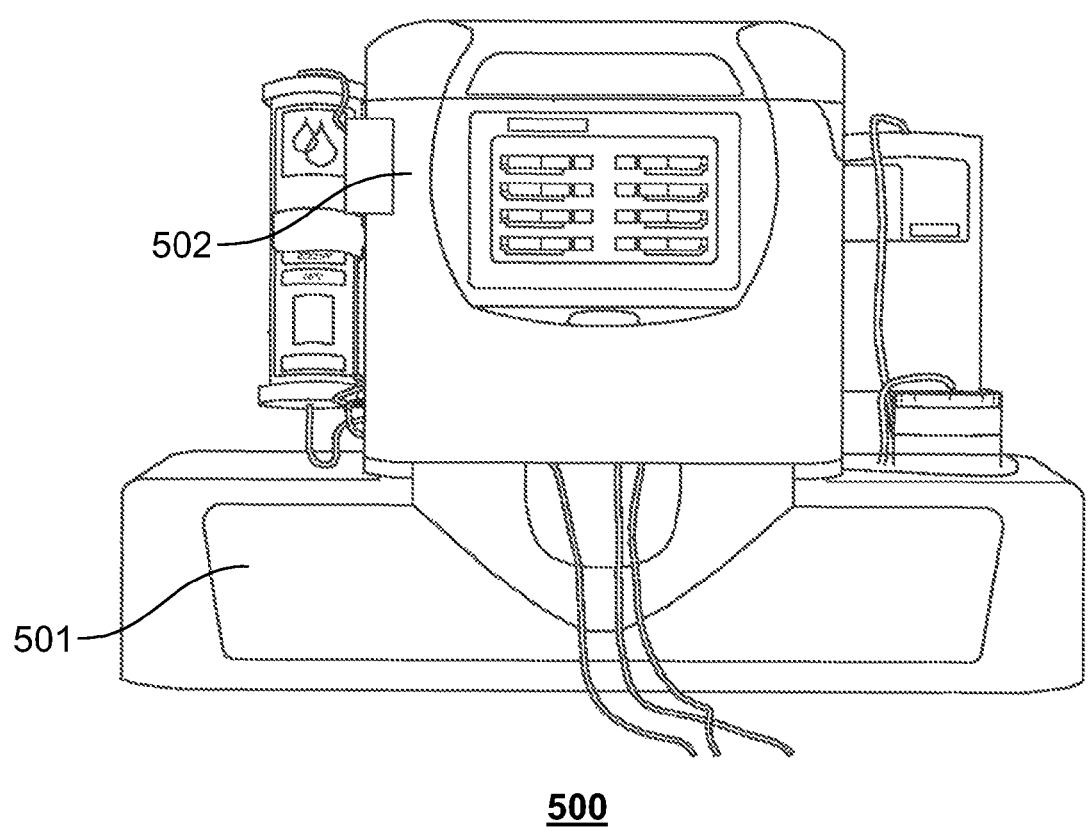
FIG. 5 illustrates an exemplary modular portable dialysis machine, which employs the reservoir subsystem of the present invention.

FIG. 5 illustrates an exemplary modular portable dialysis machine, which employs the reservoir subsystem of the present invention. Referring to FIG. 5, the dialysis machine 500 comprises two main modules—the reservoir subsystem (bottom unit) 501 and the pumping subsystem 502 (upper unit). The two modules 501 and 502 connect physically and electrically, as described earlier with reference to FIGS. 2, 3 and 4. In one embodiment, the two modules, the reservoir subsystem 501 and the pumping subsystem 502, operate in conjunction as a single unit, and not independently of each other.

Figure 6:
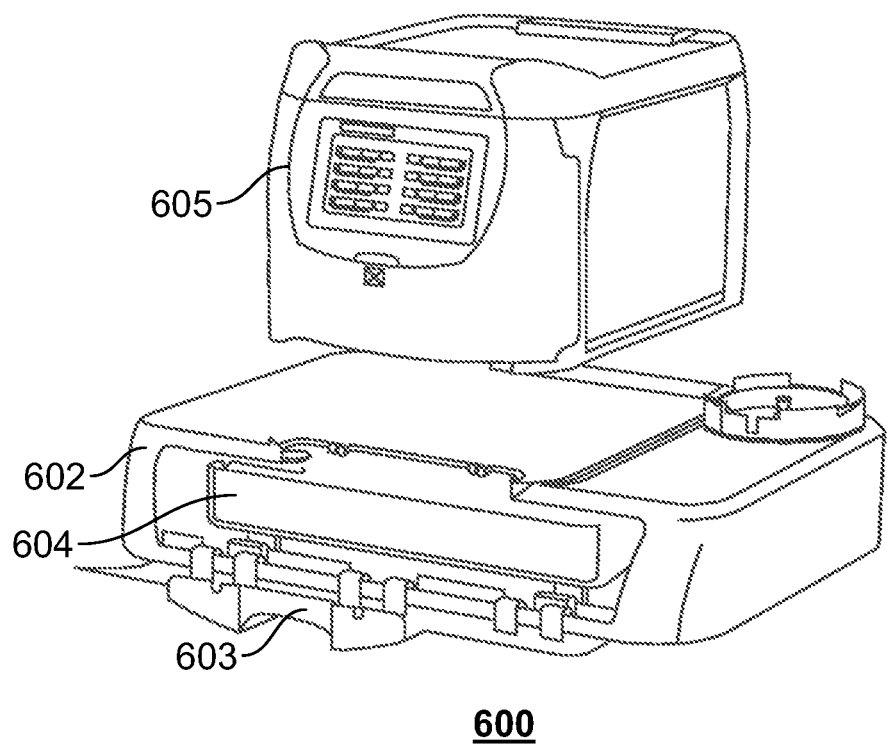
FIG. 6 provides a detailed view of the reservoir subsystem module, as used with the portable dialysis machine, according to one embodiment of the present invention.

FIG. 6 provides another view of the portable dialysis system 600 using the reservoir assembly subsystem 602 of the present invention. As can be seen from FIG. 6, the reservoir subsystem 602 is provided with a door 603, which when pulled open provides access to the fluid reservoir inside. That is, the reservoir bag (not shown) can be inserted and removed through the door opening. In one embodiment, pulling open the door 603 actuates a sensor which communicates a signal indicative of the door opening to the control unit 605. In response, the control unit 605 shuts down the dialysis process or suspends the dialysis process. In one embodiment, the door 603 is locked during the dialysis process and can only be opened by actuating a control unit 605 command to cease dialysis and open the door 603. In another embodiment, the opening of the door 603 automatically actuates a lever which causes the reservoir pan 604 to extend out from the reservoir 602. As mentioned previously, the reservoir bag is placed on a pan 604, which is itself suspended in a scale mechanism (not shown). In one embodiment, when the door 603 is pulled open, the dialysate pan 604 slides out along with the scale. The scale and pan 604 arrangement can thus be used as a measuring tray, and can be used for measuring substances other than the dialysate also, such as any packets of prescription additives that are to be added to the dialysate fluid. A button (not shown) may be provided for opening and closing the measuring tray.

Figure 7:
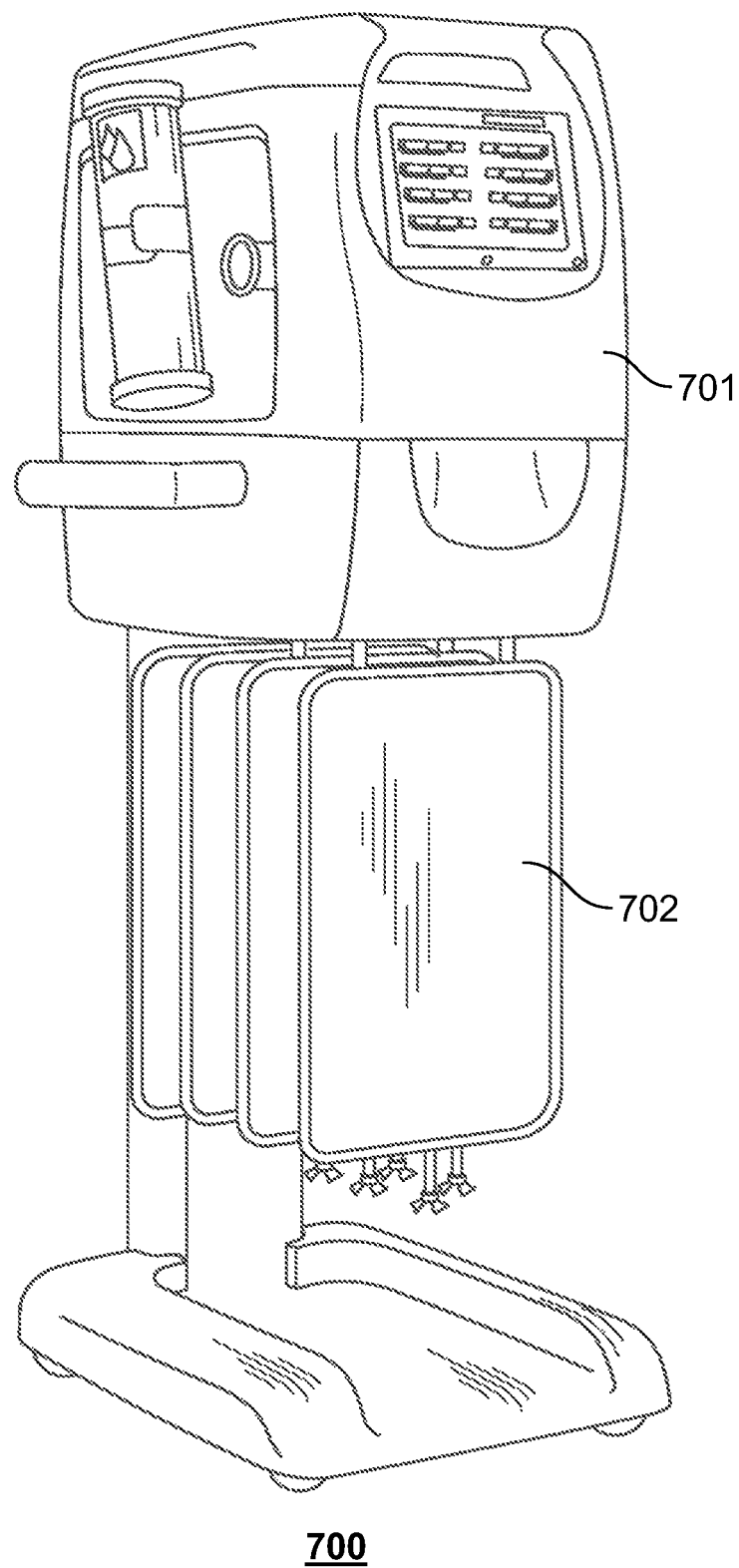
FIG. 7 illustrates another embodiment of the portable dialysis system for use in hemofiltration mode of operation.

FIG. 7 illustrates an alternate embodiment of the portable dialysis system 700 for hemofiltration or hemodialysis. Referring to FIG. 7, the machine 700 incorporates an upper subsystem (pumping unit) 701, in the same manner as illustrated in FIG. 5 with reference to 501. The system 700 however, has a different lower assembly. The lower portion of the system 700 comprises an independent bag of dialysate 702. That is, the dialysate bag is not incorporated as a part of the reservoir sub assembly. Further, the lower assembly is designed such that it incorporates a weighing mechanism (not shown) for the independent bag of dialysate 702. This arrangement is suitable when the dialysis system is configured to operate in hemofiltration mode. Since in the hemofiltration mode, various sensors used in sorbent based dialysis—such as ammonia, pH and sodium sensors are not required, therefore the entire reservoir assembly module can be removed, and the system can simply be operated using a bag of dialysate. The modular and compact design of the reservoir subsystem makes its removal easy, and simplifies the system operating in hemofiltration mode by taking away the unnecessary components. This is another advantage of integrating the major components of dialysate circuit used during hemodialysis mode into the reservoir assembly subsystem.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

We claim:

1. A reservoir module for use in a portable dialysis system comprising:
    a reservoir housing having four sides, a base, and a top, wherein said four sides, base surface, and top surface define an internal space and wherein at least one side of the top surface comprises a fluid drain gutter with a wetness sensor;
    a container adapted to contain dialysate;
    a surface located within said internal space and configured to suspend said container, wherein said surface is integrated with a scale; and
    a conductivity sensor located within said internal space, wherein said conductivity sensor comprises a coil having a plurality of turns, a capacitor in electrical communication with said coil, wherein said coil and capacitor define a circuit, and an energy source in electrical communication with said circuit.

2. The reservoir module of claim 1 wherein the energy source maintains a substantially constant voltage across said capacitor.

3. The reservoir module of claim 1 wherein said conductivity sensor outputs a value indicative of a sodium concentration in said dialysate based on an energy input required from said energy source to maintain the constant voltage across the capacitor.

4. The reservoir module of claim 1 wherein the coil has a radius between 2 and 6 inches.

5. The reservoir module of claim 4 wherein the coil generates a magnetic field.

6. The reservoir module of claim 1 wherein a heater is in thermal contact with said container.

7. The reservoir module of claim 6 wherein the heater is integrated into said surface.

8. The reservoir module of claim 1 wherein said surface comprises a plurality of flex points physically attached to said top.

9. The reservoir module of claim 1 wherein the container is an IV bag.

10. The reservoir module of claim 1 wherein a second side of the top surface comprises a second fluid drain gutter.

11. The reservoir module of claim 10 wherein the second fluid drain gutter is in fluid communication with a second wetness sensor.

12. The reservoir module of claim 1 wherein a door providing internal access to said reservoir housing is integrated into one of said four sides.

13. A module for use in an extracorporeal system comprising:
    a housing having four sides, a base, and a top, wherein said four sides, base surface, and top surface define an internal space and wherein the top surface comprises a fluid drain gutter with a wetness sensor;
    a container positioned within said internal space and adapted to contain a liquid;
    a surface located within said internal space and configured to suspend said container, wherein said surface is integrated with a scale; and
    a conductivity sensor located within said internal space.

14. The module of claim 13 wherein said conductivity sensor outputs a value indicative of an ion concentration in said liquid based on an energy input required from an energy source to maintain a constant voltage across a capacitor.

15. The module of claim 14 wherein said ion is a sodium ion.

16. The module of claim 13 wherein said conductivity sensor comprises a coil and the coil has a radius between 2 and 6 inches.

17. The module of claim 14 wherein the energy source is adapted to maintain a substantially constant voltage across said capacitor.

18. The module of claim 13 wherein the conductivity sensor further comprises an oscillator.

\* \* \* \* \*